United States Patent
Birthisel

(10) Patent No.: US 8,163,672 B2
(45) Date of Patent: *Apr. 24, 2012

(54) MULTIPLE EFFECT PLANT GROWTH PROMOTING COMPOSITION MIXTURE

(75) Inventor: Timothy D. Birthisel, Perrysburg, OH (US)

(73) Assignee: The Andersons, Inc., Maumee, OH (US)

(*) Notice: Subject to any disclaimer, the term of this patent is extended or adjusted under 35 U.S.C. 154(b) by 531 days.

This patent is subject to a terminal disclaimer.

(21) Appl. No.: 12/106,600

(22) Filed: Apr. 21, 2008

(65) Prior Publication Data

US 2008/0216536 A1 Sep. 11, 2008

Related U.S. Application Data

(63) Continuation-in-part of application No. 11/301,171, filed on Dec. 12, 2005, now Pat. No. 7,666,399.

(60) Provisional application No. 60/635,553, filed on Dec. 13, 2004, provisional application No. 60/912,722, filed on Apr. 19, 2007.

(51) Int. Cl.
*C05C 9/00* (2006.01)
*C05C 1/00* (2006.01)
*C05C 5/02* (2006.01)
*C05B 7/00* (2006.01)
*C05B 17/00* (2006.01)

(52) U.S. Cl. ............ 504/101; 71/28; 71/29; 71/30; 71/32; 71/33; 71/34; 71/54; 71/58; 71/59; 71/60; 71/63

(58) Field of Classification Search .......... 504/101; 71/28, 29, 30, 32, 33, 34, 54, 58, 59, 60, 71/63

See application file for complete search history.

(56) References Cited

U.S. PATENT DOCUMENTS

| 5,174,804 A * | 12/1992 | Rehberg et al. ............... 504/101 |
| 5,518,517 A | 5/1996 | Jahnke et al. |
| 6,479,062 B2 | 11/2002 | Vander Hooven |
| 7,635,404 B1 * | 12/2009 | Devic et al. ...................... 71/11 |
| 2002/0173565 A1 | 11/2002 | Blount |

FOREIGN PATENT DOCUMENTS

| JP | 405221801 A | 8/1993 |
| JP | 407109192 A | 4/1995 |
| JP | 020003136585 A | 11/2000 |
| JP | 02001048705 A | 2/2001 |

OTHER PUBLICATIONS

A. O. Leedahl et al, "Application of Pesticides On-The-Go with Granular Fertilizer", Pesticide Formulations and Application Systems: International Aspects, 9$^{th}$ Volume, ASTM STP 1036, James L. Hazen and David A. Hovde, Eds., American Society for Testing and Materials, Philadelphia (1989), 204-208.*

Azom.com, Particle Size—US Sieve Series and Tyler Mesh Size Equivalents, http://www.azom.com/details.asp?ArticleID=1417, Nov. 9, 2004.

* cited by examiner

*Primary Examiner* — Wayne Langel
(74) *Attorney, Agent, or Firm* — Patent Procurement Services

(57) ABSTRACT

A multiple effect plant growth promoting mixture is provided that includes a first plurality of fertilizer granules, each containing a quantity of a bioavailable source of nitrogen, phosphorus, or potassium. A second plurality of granules, each containing an active agent effective in inhibiting an organism interfering with plant growth are intermixed with the fertilizer granules. The fertilizer granules are substantially devoid of the active agent adhering to the fertilizer granule and the active agent granules are substantially devoid of fertilizer. The potential for cross contamination being associated with granule breakage associated with intermixing and transport.

39 Claims, No Drawings

MULTIPLE EFFECT PLANT GROWTH PROMOTING COMPOSITION MIXTURE

RELATED APPLICATIONS

This application is a non-provisional application that claims priority benefit of U.S. Provisional Application Ser. No. 60/912,722 filed on 19 Apr. 2007; and is a continuation-in-part of U.S. patent application Ser. No. 11/301,171 filed 12 Dec. 2005 which in turn claims priority of U.S. Provisional Patent Application Ser. No. 60/635,553 filed Dec. 13, 2004; the contents of which are hereby incorporated by reference.

FIELD OF THE INVENTION

The present invention relates in general to a mixture of fertilizer granules and active agent carrying granules to promote plant growth and in particular to such a granule mixture in which the different types of granules operate without cross interference to simultaneously deliver plant growth fertilizer and an active agent to inhibit an organism interfering with plant growth.

BACKGROUND OF THE INVENTION

A continuing problem in care of large areas of cultivated vegetation is the difficulty of delivery of an agent such as a plant nutrient, fertilizer or a pesticide to the target. A practical and labor-saving approach to agent delivery in areas such as golf courses, parks, lawns, gardens and woodlands has been broadcast application of granular products containing an agent, for example via rotary spreader. Using granular products having particle sizes in the range of about 0.5 millimeter to about 10 millimeters, an operator can cover a large area with minimal distance traversed by the spreader itself, while applying the granular products relatively uniformly to the desired area.

A further efficiency of labor is realized when multiple substances useful to promote plant growth are applied simultaneously. Efforts to provide for simultaneous application of fertilizer and pesticide have resulted in a particle formulated to contain both fertilizer and pesticide components. U.S. Pat. Nos. 5,783,203; 5,830,576; 6,221,375 B1; 6,387,388 B1; 6,436,421 B1; and 7,018,643 B2 are exemplary of these efforts.

Unfortunately, the production of a dual action fertilizer-pesticide particle has proven to be only partially successful as a result of phytotoxic chemical burning associated with a hygroscopic fertilizer making a particle adherent towards foliage inducing phytotoxicity through pesticide exposure. Additionally, to manufacture such a particle is complicated owing to regulatory, seasonal, complicated production process requirements, and customer preferences as to the N-P-K fertilizer composition as well as differing environmental targets and/or treated area distribution requirements between components of the desired formulation. As a result, specialized batches of dual action single particles are problematic in tailoring variations based on the specific plant growth environment, infestations, or the like. These variations are either not met or create inventory problems and increase the cost of production.

Thus, there exists a need for a multiple effect mixture of different granule types to provide for the efficient broadcast of fertilizer and an active agent within a simple application while providing a simplified manufacturing and distribution process.

SUMMARY OF THE INVENTION

A multiple effect plant growth promoting mixture is provided that includes a first plurality of fertilizer granules, each containing a quantity of a bioavailable source of nitrogen, phosphorus, or potassium. A second plurality of granules, each containing an active agent effective in inhibiting an organism interfering with plant growth are intermixed with the fertilizer granules. The fertilizer granules are substantially devoid of the active agent adhering to the fertilizer granule and the active agent granules are substantially devoid of fertilizer. The potential for cross contamination being associated with granule breakage associated with intermixing and transport.

DETAILED DESCRIPTION OF THE PREFERRED EMBODIMENTS

The present invention has utility as a mixture promoting plant growth through multiple modes, and specifically includes the simultaneous application of multiple fertilizer granules substantially independent of an active agent in concert with the delivery of multiple active agent granules mixed therewith where the active agent granules are substantially independent of fertilizer. The combination of fertilizer granules and active agent(s) granules in a single mixed composition allows for a single broadcast application to deliver fertilizer and one or more active agent(s) inhibitive of an organism interfering with plant growth, or causing growth regulation, or the like thereby saving on labor of application. Additionally, as the granules are substantially devoid of dust cross contamination allowing them to operate without interference from the to the intermixed granule. In contrast to the prior art where fertilizer and pesticide have been formulated as a single unified particle, the combination of the present invention promotes ease of manufacture in allowing bulk production of fertilizer granules separate from active agent granules and the separate storage of each with custom blending of the two types of granules in response to custom needs associated with regulatory usage of particular active agents, a deleterious organism outbreak, seasonal conditions, soil nutrient depletion, or any combination thereof. Additionally, with the reduced processing associated with modifying a fertilizer granule to include a pesticide and instead only mixing two types of fully formulated granules together, an inventive mixture shows less granule dusting and fragmentation associated with handling. As a result, the usage of inert adhesion and dusting agents conventional to the art to promote particle integrity is eliminated or at least greatly diminished, thereby affording ease of manufacture and higher efficacy through avoidance of unintended chemical or physical interactions between inert ingredients, various plant nutrients, active agent(s) and granule mixtures under application conditions. It is appreciated that the tolerance of a specific composition of fertilizer or active agent granule to cross contamination is readily determined through routine experimentation and the nature of the mode of action. For instance, pest attractant containing active agent granules are diminished by adherence of a quantity of fertilizer making the active agent granules less active to pests. Through control of the specific identity of the fertilizer in the fertilizer granule and the quantity of fertilizer adherent tot the active agent granules through routine experimentation, a pest attractant in an active agent granule remains attractive to pests thereby bringing the pest into contact with the toxic agent and in so doing reduces the overall quantity of toxin needed in the active agent.

A fertilizer granule operative in the present invention need only be well sized for broadcast distribution and inert towards active agent granules mixed therewith for broadcast distribution. A typical fertilizer granule has a size of from 500 to 3,000 microns. The fertilizer granule includes a quantity of a bioavailable source of nitrogen, phosphorus, potassium, or a combination thereof. The bioavailable N-P-K ingredients are present in the fertilizer granule in an amount ranging from 5 to 99 weight percent of the total dry weight of the fertilizer granules. More preferably, the N-P-K components are present in amounts ranging from 30 to 99 percent by weight of the dry weight of fertilizer granules. Still more preferably, the N-P-K components are present in amounts ranging from 50 to 99 percent by weight of the total dry weight of the fertilizer granules.

Exemplary fertilizer N-P-K contributing constituents contain one of the plant nutrients nitrogen, phosphate or potassium and illustratively include urea, sulfur-coated urea, isobutylidene diurea, ammonium nitrate, ammonium phosphates varying degrees of ammonation, ammonium polyphosphates, triple super phosphate, phosphoric acid, potassium sulphate, potassium nitrate, potassium metaphosphate, potassium chloride, dipotassium carbonate, potassium oxide, phosphate rock, nitrophosphate, and a combination of these. It is also appreciated that a fertilizer granule readily incorporates other substances stimulative of target plant growth and illustratively include soil conditioners, trace elements, plant hormones active in the target plant, and dust control, flowability and/or storability additives. Additionally, the fertilizer granule optionally includes conventional fillers, binders, and additives as exemplified in U.S. Pat. No. 6,884,756. Preferably, the fertilizer granule includes at least 20 units of N-P-K nutrients, where a "unit" is used herein to define an increment of 1% of a guaranteed plant nutrient as defined by the American Association of Plant Food Control Officials (AAPFCO), which is the uniform standards-setting association of state fertilizer control officials in the United States.

A binder component is present in a carrier particle an amount ranging from 0.1% to 75% by weight of the total dry weight of the carrier particle. In a further embodiment, the binder component is present in an amount ranging from 1% to 25% by weight of the total dry weight of the particle. A binder component is included in a particle as necessary to produce or promote cohesion in forming a particle capable of retaining a specified form during transport and/or distribution. A binder component may be bentonite clay, carbohydrate, protein, lipid, synthetic polymer, glycolipid, glycoprotein, lipoprotein, lignin, a lignin derivative, a carbohydrate-based composition, and a combination thereof. In a preferred embodiment the binder component is a lignin derivative and is optionally calcium lignosulfonate. Alternatively, the binder component is selected from the group consisting of: a monosaccharide, a disaccharide, an oligosaccharide, a polysaccharide and combinations thereof. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxymethylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

An inventive fertilizer granule is produced by a number of processes. In the preferred process, the granule components are wet-granulated through a process of steps, including mixing of various dry components, wet-massing the dry powder mixture with liquid surfactants, binders or the like, alone or with the addition of a solvent to arrive at a suitable consistency for granulating. Of the binders detailed herein, methyleneurea is particularly preferred.

In order to preclude undesirable inventive mixture interactions, a fertilizer granule is substantially devoid of an active agent. Prior art interactions associated with single particles containing both fertilizer and the pesticide have included chemical foliage burning when such single particles are applied under high humidity, high temperature conditions.

As used herein "substantially devoid" is defined to mean that the interior of a granule is formulated free from a given substance and that surface adhesion of dust associated with the given substance amounts to less than 20% of the total dry weight of the granule, preferably less than 10% of the total dry weight, more preferably less than 5% of the total dry weight and most preferably, less than 1% of the total dry weight. For example, a fertilizer granule if formulated devoid of active agent and most preferably less than 1% of the active agent present as active agent granules intermixed with the fertilizer granules becomes adhered to fertilizer granules.

An active agent granule carrier particle operative in the present invention need only be well sized for broadcast distribution and be inert towards the active agent coating. Typically, a base carrier particle has a size from 500 to 3000 microns. Suitable carrier particles include fragmented materials such as rock dust, clay, corncob, cereal or grain hulls, peanut hulls, plant pulp, other plant-based cellulosic materials, clays, and granular baits. The carrier component is specifically excluded from the definition of a fertilizer as used herein with respect to the present invention.

Specific examples of base carrier particles include: limestone particulate having a mean particle size of 1000 microns; processed snack food; and defatted, extruded corn granules having a mean particle size of 1500 microns. Alternatively, a carrier particle is formed through the combination of a binder component with fine grain particle as detailed above and has 90% of the particles having a diameter less than 150 microns. Particulate is typically present from 0.1 to 99.9 total weight percent and preferably from 5 to 98 total weight percent. An exemplary composite carrier particle is disclosed in U.S. Pat. No. 6,884,756.

A binder component is present in an active agent carrier particle in an amount ranging from 0.1 percent to 75 percent by weight of the total dry weight of the active agent granule. In a further embodiment, the binder component is present in an amount ranging from 1 percent to 25 percent by weight of the total dry weight of the active agent granule. An active agent binder component is included in an active agent granule as necessary to produce or promote cohesion in forming the granule capable of retaining a specified form during transportation and/or distribution. The identity of a binder component is the same as the binder components detailed with respect to a fertilizer granule where these binders are specifically excluded from the definition of a fertilizer as used herein with respect to the present invention.

Optionally, the active agent granule incorporates a pest attractant. In an active agent granule incorporating a pest attractant, the pest attractant is present in an amount ranging from 0.05% to 50% by weight of the total dry weight of the carrier particle. In a more preferred embodiment, the pest attractant active ingredient is present in an amount ranging from 0.1% to 30% by weight of the total dry weight of the particle.

Pest attractants are foodstuffs, scents, or pheromones attractive to a target pest. It is appreciated that when a pest attractant is a scent or pheromone the amounts needed are quite small and typically range from 0.0001 to 0.05 total weight percent of an inventive granule. The nature of the pest attractant foodstuff, scent, or pheromone is readily selected by reviewing the existing literature as to pest diet, and sexual hormones. Representative of the literature is "Destructive Turfgrass Insects: Biology, Diagnosis, and Control" by D. A. Porter (1995).

An active agent in solid or liquid form is present in or on an active agent granule. The active agent is added virtually without limit and includes any active agent solid or liquid active to inhibit an organism deleterious to the target plant and includes herbicide, insecticide, fungicide, growth regulator, nematicide, or other biologically active agent or pesticide. Representative herbicide active agents illustratively include dinitroanilines such as benefin, trifluralin, pendimethalin, and prodiamine; oxadiazoles such as oxadiazon; triazines such as atrazine and simazine; triazolinones such as carfentrazone and sulfentrazone; aryloxyphenoxy propionates; arylaminopropionic acid; cineole (such as cinmethylin); cyclohexanediones; sulfonylureas such as trifloxysulfuron and metsulfuron-methyl; imidazolinones; pyrimidinylthio-benzoate; triazolopyrimidine; pyridazine; phenoxys (or phenoxies); benzoic acids; carboxylic acids (such as DCPA, clopyralid, trichloroacetic acid, and fluoroxypyr); quinoline carboxylic acid; semicarbazone; triazinones; uracils; pyridazinone; phenyl-carbamates; nitriles; benzothiadiazoles; organoarsenicals; phenyl-pyridazine; triketones such as mesotrione; ureas and substituted ureas (such as diuron, linuron, siduron, tebuthiuron, dymron etc.); amide (such as propanil and bromobutide); thiocarbamates; pyrazolium (such as difenzoquat); phosphoric acid compounds (such as glufosinate-ammonium and glyphosate); triazole; pyridazinone; nicotinanilide; pyridinone (such as fluridone); isoxazolidinone; diphenylethers; N-phenylphthalimides; oxadiazole; triazolinone; chloroacetamides; oxyacetamides; phthalamate; phthalamate semicarbazone; nitrile; N-phenylphthalimides; oxadiazole; triazolinone; acetamides; benzoylisoxazole; isoxazole; pyrazole; pyrazolium; triketone; and benzofuran; various ALS inhibitors; and plant extract herbicides such as the allelopathic exudates of various plants.

Representative microbiocidal and fungicidal active agents illustratively include plant and general disease control agents including fungicides, fungistats, antibiotics and bacteriocides of the following chemical families and functional groupings; various acetamides, sterol inhibitors or demethylase inhibitors, dicarboximides (such as iprodione), phthalides, phthalmic acids, triadiazoles, isophthalates, triazines, triconazoles, strobilurins, benzimidazoles, benzithiazoles, dithiocarbamates, carboxamides, carboxides or anilides, chlorphenyls, indolecarboxylic acids, isoxazoles, imidazoles, oxazolinediones, guanidines, diguanidines, piperidines, pyridines, sulfenamides, sulfonamides, quinolines, cyanoimidazoles, pyrazoles, pyrrolecarbonitriles, spiroketalamines, thiazoles, various chemical families of oomycete (pythium) fungicides, nitriles, chlorinated hydrocarbons, phenylpyrroles, polyoxins, pyridazinones, mycotoxins (e.g. penicillin) or other antibiotics (e.g. streptomycin, kasugamycin, blasticidin, polyoxins, validamycin, mildiomycin, and oxytetracyline), morpholines, other organic compounds such as piperalin, piperazine derivatives and tolylfluanid, bronopol, organic compound mixtures (e.g. bacticin and harpin protein), organic acids such as cinnamic acid and its derivatives, bacteria such as *Agrobacterium radiobacter*, *Bacillus subtilus*, *Erwinia carotovora*, *Pseudomonas flourescens* and *P. chlorophis*, and any varieties or strains thereof, fungi such as *Candida oleophila*, *Fusarium*, *Tricoderma*, *Gliocladium*, *Streptomyces*, and *Ampelomyces* and any species, varieties or strains thereof, and viruses such as tomovax.

For purposes of this invention, plant growth regulators are ingredients such as trinexepac-ethyl, gibberellic acid, gibberellins, cytokinins, benzyladenine, glycines, quinolenes, phosphoric acid compounds, organic carbamates, quaternary ammonium compounds, acetamides, ethychlozate, azoles, paclobutrazol, anilides, pyradazidine, pyrimidines, napthaleneacetamide, phthalmides, phenoxies, pyrimidines, hybridizing agent, biostimulants, seaweed extracts and herbicides (typically at low use rates), phthalmides, phenoxies, organic or carboxylic acids (e.g. gamma amino butyric acid and L-glutamic acid, naphthalene acetic acid, clofencoet, sintofen, nicotinic acids), and herbicides (typically at low use rates).

For purposes of this invention, other pesticides include animal and bird repellants, bitter flavors, irritants, and malodorous ingredients, molluscicides (e.g., slugs and snails), nematicides, rodenticides, defoliants, chemosterilants, plant defense boosters (harpin protein and chitosan) desiccants (may also be used as a harvest aid), and other beneficial or detrimental agents applied to plant or other surfaces.

Pesticides suitable to form a liquid coating on an active agent carrier particle include pyrethroids such as bifenthrin, permethrin, deltamethrin, lambda cyhalothrin, cyfluthrin, or betacyfluthrin; organophosphates such as chlorpyrifos and trichlorfon; limonoids such as azadirachtin or meliartenin; phenyl pyrazoles or oxadiazines such as indoxacarb; phthallic acid diamides such as flubendiamide and anthranilic diamides; neonicitinoids such as imidacloprid and clothianidin, and diacylhadrazines such as halofenozide; and carbamates such as carbaryl and indoxacarb. Additionally, it is appreciated that a number of conventional adjuvant systems used to solubilize a pesticide for application as a coating onto an active agent carrier particle are rendered more effective by the present invention. By way of example, pyrethroids degrade to yield organic acids that in proximity to certain pesticide powders such as carbamates function to extend the carbamate activity half-life.

For purposes of this invention, other protectants and beneficial ingredients include attractants, baits, herbicide safeners, antidessicants, antitranspirants, frost prevention aids, inoculants, dyes, brighteners, markers, synergists, pigments, UV protectants, antioxidants, leaf polish, pigmentation stimulants and inhibitors, surfactants, moisture retention aids, molluscicides (e.g., slugs and snails), nematicides, rodenticides, defoliants, desiccants, sticky traps, and IPM lures.

It is appreciated that multiple active agents are readily formulated within an active agent granule. Preferably, synergistic combinations of active agents such as two pesticides that have complementary modes of action such that the total amount of the multiple active agents needed to provide a given level of organism inhibition interfering with plant growth is reduced relative to the active agent administered separately. Active agent granules are optionally compounded with inner fillers, dust control and flow aids, solvents, surfactants, and/or other adjuvants, alone or in combination with up to several other active agents.

A collection of fertilizer granules and active agent granules are preferred each formulated such the density difference between fertilizer granules and active agent granules is less than 1000%. More preferably, the density difference between fertilizer granules and active agent granules is lass than 500%. It is appreciated that by controlling the density difference, the propensity of the mixture to segregate during transit is reduced. Settling is also disfavor in a mixture of fertilizer granules and active agent granules that vary in average diameter by less than 30 diameter % and preferably, less than 10 diameter %.

The mixture that is made up of fertilizer granules varies between 10 and 99 number % of the granules present. Active agent granules vary between 0.0005 and 90 number percent with the inclusion of an inert carrier particle akin to an active agent granule less the active agent is also considered to be part of the present invention. Inert granules making up from 0 to 30 number percent of the particles present.

The inventive mixture affords a formulator the ability to maintain separate stocks of fertilizer and or active agent granules and blend fertilizer granules and active agent granules in response to customer orders, or field conditions. As a result an inventive mixture is broadcast onto soil surrounding a target plant with specificity as to factors such as soil chemistry, interfering organism outbreaks, rainfall, drought, or the like.

A fertilizer granule is readily formed by conventional techniques or purchased commercially, e.g., Andersons Golf Products Turf Fertilizer 18-6-15 (The Andersons, Maumee, Ohio). Techniques commonly used to form a fertilizer granule containing fertilizer and any other optional adjuvants illustratively includes drum or pan agglomeration, pastille formation, molten droplet spray, crystallization, extrusion, and compaction. Techniques for the formation of a fertilizer pellet are provided in Granulated Fertilizers, Robert A. Hendrie, Noyes Data Corporation, Park Ridge, N.J., 1976. Other techniques include those disclosed in Example A of U.S. Pat. No. 6,884,756.

An active agent granule is readily formed by conventional techniques or purchased commercially (The Andersons, Maumee, Ohio). Such techniques are detailed in U.S. Pat. No. 6,231,660.

The mixing of fertilizer granules and active agent granules occurs through conventional techniques with preference to mixing technologies that provide minimized granule fracture and dusting. Mixing techniques operative herein illustratively include mechanical, air, spraying, and tumbling. It is appreciated that fertilizer granule stock and active agent granule stock are readily stored separately and blended in response to a particular order. Alternatively preselected mixtures of fertilizer granules and active agent granules are bagged and stored.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A multiple effect plant growth promoting mixture comprising in combination:
   a first plurality of fertilizer granules each containing a quantity of a bioavailable source of an element selected from the group consisting of: nitrogen, phosphorus, and potassium; and
   a second plurality of granules, each of said second plurality of granules containing an active agent of a herbicide wherein said first plurality of fertilizer granules are substantially independent of said active agent and said second plurality of granules are substantially devoid of the bioavailable source of the element.

2. The mixture of claim 1 wherein said first plurality of fertilizer granules have an average size of from 500 to 3000 microns.

3. The mixture of claim 2 wherein said second plurality of granules have an active agent granule average diameter within 30 diameter percent of the average fertilizer granule diameter.

4. The mixture of claim 2 wherein said second plurality of granules have an active agent granule average diameter within 10 diameter percent of the average fertilizer granule diameter.

5. The mixture of claim 1 wherein said first plurality of fertilizer granules further comprise a binder.

6. The mixture of claim 1 wherein said second plurality of granules each further comprise a second active agent.

7. The mixture of claim 6 wherein said second active agent acts synergistically with said active agent in inhibiting the organism interfering with plant growth.

8. The combination of claim 1 wherein said first plurality of fertilizer granules are present as 10 to 99.9 granule number percent of the combination.

9. The mixture of claim 7 wherein said second active agent is present as a powder and said active agent is present as a dried liquid coating.

10. A process for promoting plant growth comprising:
    broadcast distributing the mixture of claim 1 to soil surrounding the plant.

11. The process of claim 10 further comprising tailoring the combination of said plurality of fertilizer granules and said second plurality of granules based on condition of the plant prior to the broadcast distribution.

12. The mixture of claim 1 wherein the herbicide is a benefin, trifluralin, or pendimethalin.

13. The mixture of claim 1 wherein the herbicide is an oxadiazole.

14. The mixture of claim 1 wherein the herbicide is a triazine or a triazolinone.

15. The mixture of claim 1 wherein the herbicide is an aryloxyphenoxy propionate or an arylaminopropionic acid.

16. The mixture of claim 1 wherein the herbicide is an cineole.

17. The mixture of claim 1 wherein the herbicide is trifloxysulfuron or metsulfuron-methyl.

18. The mixture of claim 1 wherein the herbicide is pyrimidinylthio-benzoate.

19. The mixture of claim 1 wherein the herbicide is one of triazolopyrimidine, pyridazine, clopyralid, trichloroacetic acid, or flouroxypyr.

20. The mixture of claim 1 wherein the herbicide is one of pyridazinone, a phenyl-carbamates, a benzothiadiazoles, an organoarsenicals or a phenyl-pyridazine.

21. The mixture of claim 1 wherein the herbicide is mesotrione diuron, linuron, siduron, tebuthiuron, dymron, propanil or bromobutide.

22. The mixture of claim 1 wherein the herbicide is one of a thiocarbamates, difenzoquat, glufosinate-ammonium; glyphosate triazole; pyridazinone; nicotinanilide; fluridone; isoxazolidinone; diphenylethers; N-phenylphthalimides; oxadiazole; triazolinone; chloroacetamides; oxyacetamides; phthalamate; phthalamate semicarbazone; nitrile; N-phenylphthalimides; oxadiazole; triazolinone; acetamides; benzoylisoxazole; isoxazole; pyrazole; pyrazolium; triketone; benzofuran; plant extract herbicides.

23. The mixture of claim 1 wherein the herbicide is one of triazole, pyridazinone, nicotinanilide, fluridone, or isoxazolidinone.

24. The mixture of claim 1 wherein the herbicide is one of a diphenylethers, a or a N-phenylphthalimides.

25. The mixture of claim 1 wherein the herbicide is one of oxadiazole, triazolinone, a chloroacetamides, an oxyacetamides, phthalamate, phthalamate semicarbazone, benzoylisoxazole, isoxazole, pyrazole, pyrazolium; or benzofuran.

26. A multiple effect plant growth promoting mixture comprising in combination:
a first plurality of fertilizer granules each containing a quantity of a bioavailable source of an element selected from the group consisting of: nitrogen, phosphorus, and potassium; and
a second plurality of granules, each of said second plurality of granules containing an active agent of an insecticide wherein said first plurality of fertilizer granules are substantially independent of said active agent and said second plurality of granules are substantially devoid of the bioavailable source of the element.

27. The mixture of claim 26 wherein the insecticide is a pyrethroid.

28. The mixture of claim 26 wherein the insecticide is a neonicitinoid or a diacylhydrazine.

29. The mixture of claim 26 wherein the insecticide is a compound selected from the group consisting of: an organophosphate, a liminoid, a phenylpyrazole, an oxadizine and a phthallic acid diamide.

30. The mixture of claim 26 wherein said first plurality of fertilizer granules have an average size of from 500 to 3000 microns.

31. The mixture of claim 30 wherein said second plurality of granules have an active agent granule average diameter within 30 diameter percent of the average fertilizer granule diameter.

32. The mixture of claim 30 wherein said second plurality of granules have an active agent granule average diameter within 10 diameter percent of the average fertilizer granule diameter.

33. The mixture of claim 26 wherein said first plurality of fertilizer granules further comprise a binder.

34. The mixture of claim 26 wherein said second plurality of granules each further comprise a second active agent.

35. The mixture of claim 34 wherein said second active agent acts synergistically with said active agent in inhibiting the organism interfering with plant growth.

36. The combination of claim 26 wherein said first plurality of fertilizer granules are present as 10 to 99.9 granule number percent of the combination.

37. The mixture of claim 36 wherein said second active agent is present as a powder and said active agent is present as a dried liquid coating.

38. A process for promoting plant growth comprising:
broadcast distributing the mixture of claim 26 to soil surrounding the plant.

39. The process of claim 38 further comprising tailoring the combination of said plurality of fertilizer granules and said second plurality of granules based on condition of the plant prior to the broadcast distribution.

\* \* \* \* \*